(12) United States Patent
Malin

(10) Patent No.: US 10,124,341 B2
(45) Date of Patent: Nov. 13, 2018

(54) LOW-TEMPERATURE STORAGE DEVICE WITH CASSETTE HANDLER

(71) Applicant: LICONIC AG, Mauren (LI)

(72) Inventor: Cosmas G. Malin, Mauren (LI)

(73) Assignee: LICONIC AG, Mauren (LI)

( * ) Notice: Subject to any disclaimer, the term of this patent is extended or adjusted under 35 U.S.C. 154(b) by 178 days.

(21) Appl. No.: 14/860,135

(22) Filed: Sep. 21, 2015

(65) Prior Publication Data

US 2016/0082440 A1 Mar. 24, 2016

(30) Foreign Application Priority Data

Sep. 22, 2014 (CH) ...................................... 1429/14

(51) Int. Cl.
| | | |
|---|---|---|
| *B01L 7/00* | (2006.01) | |
| *G01N 1/42* | (2006.01) | |
| *B01L 9/06* | (2006.01) | |
| *F25D 13/06* | (2006.01) | |
| *F25D 25/04* | (2006.01) | |

(52) U.S. Cl.
CPC ............... *B01L 7/50* (2013.01); *B01L 9/06* (2013.01); *F25D 13/06* (2013.01); *F25D 25/04* (2013.01); *G01N 1/42* (2013.01); *B01L 2200/18* (2013.01); *B01L 2300/02* (2013.01); *B01L 2300/1894* (2013.01)

(58) Field of Classification Search
CPC ..... B01L 7/50; B01L 2300/1894; G01N 1/42; F25D 13/06; F25D 25/04; H01F 2007/208
See application file for complete search history.

(56) References Cited

U.S. PATENT DOCUMENTS

| | | | |
|---|---|---|---|
| 2,165,513 A * | 7/1939 | Smith .................... | F25D 13/02 312/312 |
| 5,038,128 A * | 8/1991 | Georgiev ................. | B66C 1/04 294/65.5 |
| 5,240,139 A | 8/1993 | Chirnomas | |
| 5,435,685 A | 7/1995 | Tsuda et al. | |
| 5,470,744 A | 11/1995 | Astle | |
| 7,527,764 B2 | 5/2009 | Angelantoni et al. | |
| 7,544,329 B2 * | 6/2009 | Malin .................... | C12M 23/50 422/430 |
| 9,255,936 B2 * | 2/2016 | Hunt .................... | A01N 1/0236 |
| 2003/0233842 A1 | 12/2003 | Junca et al. | |
| 2004/0115101 A1 | 6/2004 | Malin | |

(Continued)

FOREIGN PATENT DOCUMENTS

| | | |
|---|---|---|
| CH | 708 425 | 2/2015 |
| EP | 1 972 874 | 9/2008 |
| JP | 2005-143873 | 6/2005 |

OTHER PUBLICATIONS

EP Search Report dated Feb. 2, 2016 issued in EP application 15002720.9.

*Primary Examiner* — Christopher R Zerphey
(74) *Attorney, Agent, or Firm* — Greenblum & Bernstein, P.L.C.

(57) ABSTRACT

The storage device is adapted to store a plurality of objects, such as sample tube holders, at low temperatures, e.g. at −80° C. It comprises a storage chamber with a plurality of storage cassettes arranged in its bottom section. A cassette lift in its top section can be used to lift individual storage cassettes up and to move them to an access opening, where the contents of the storage cassette can be accessed.

20 Claims, 7 Drawing Sheets

(56) References Cited

U.S. PATENT DOCUMENTS

| | | | |
|---|---|---|---|
| 2006/0150659 A1* | 7/2006 | Sidor | F25D 13/06 |
| | | | 62/378 |
| 2006/0156753 A1 | 7/2006 | Fuhr et al. | |
| 2008/0231152 A1 | 9/2008 | Malin | |
| 2008/0260511 A1 | 10/2008 | Fattinger | |
| 2009/0026905 A1* | 1/2009 | Malin | B65G 1/0407 |
| | | | 312/400 |
| 2010/0183408 A1 | 7/2010 | Malin | |
| 2010/0275636 A1 | 11/2010 | Yoshimura et al. | |
| 2011/0219788 A1 | 9/2011 | Zimmermann et al. | |
| 2012/0060514 A1 | 3/2012 | Warhurst | |
| 2012/0060520 A1* | 3/2012 | Collins | A01N 1/0236 |
| | | | 62/62 |
| 2012/0060539 A1 | 3/2012 | Hunt et al. | |
| 2012/0060541 A1 | 3/2012 | Hunt et al. | |
| 2012/0134897 A1 | 5/2012 | Malin | |
| 2014/0190977 A1 | 7/2014 | Malin | |

\* cited by examiner

LOW-TEMPERATURE STORAGE DEVICE WITH CASSETTE HANDLER

CROSS REFERENCES TO RELATED APPLICATIONS

This application claims the priority of Swiss patent application 1429/14, filed Sep. 22, 2014, the disclosure of which is incorporated herein by reference in its entirety.

TECHNICAL FIELD

The invention relates to a low-temperature storage device for storing a plurality of objects at a temperature of less than 0° C., in particular below −20° C., typically at approximately −80° C.

BACKGROUND ART

Storage devices of this type are e.g. used to store a large number of biological samples at low temperatures. Such samples are e.g. stored in tubes, which in turn are arranged in tube holders. Such tube holders can e.g. be held in storage cassettes.

A device of this type is described in US 2003/0233842. It comprises a storage chamber having a bottom section and a top section. The bottom section forms a cassette store having a plurality of cassette locations. Each such location holds one storage cassette.

A cassette handler with a cassette lift is located in the top section of the storage chamber. The cassette lift is adapted to lift individual cassettes from their cassette location to an elevated position, where a spatula removes or inserts one object (e.g. tube holder) from/into the storage cassette. After this operation, the cassette is lowered back into its cassette location.

DISCLOSURE OF THE INVENTION

The object of the present invention is to provide a low-temperature storage device of the type above that that allows to efficiently handle the objects in the storage cassettes.

Accordingly, the device comprises:

A storage chamber having a bottom section and a top section. This is the chamber where the objects are stored.

A refrigerator device adapted and structured to cool said storage chamber to a storage temperature below 0° C., in particular below −20° C. This device is used to cool the objects to their storage temperature.

Vertical, insulating walls enclosing said storage chamber. The storage chamber is insulated, and this insulation comprises said vertical walls.

A transfer location arranged outside said storage chamber. This is the location that at least temporarily holds the objects that are to be moved into the storage chamber or that have been removed from the storage chamber.

An access opening arranged in at least one of said insulating walls between said storage chamber and said transfer location. The objects pass this access opening on their way between the storage chamber and the transfer location.

A cassette store arranged in said bottom section of said storage chamber and forming a plurality of cassette locations. This is the location where the storage cassettes are stored.

A plurality of storage cassettes arranged beside each other in said cassette locations. Each storage cassette comprises a plurality of storage locations arranged vertically above each other, and each such storage location is structured and adapted to receive at least one of said objects. In other words, the objects are stored in locations above each other in said cassettes, such that a plurality of objects can be handled simultaneously in a single cassette.

A cassette handler located in said storage chamber comprising a) a cassette lift to move an individual storage cassette between its cassette location and said top section and b) a cassette holder adapted and structured to hold a cassette raised by the cassette lift in a raised position in said top section, c) a transport mechanism to horizontally displace said cassette holder with a raised cassette, between a position where said raised cassette is vertically above its cassette location to an access position where said raised cassette is adjacent to said access opening.

The cassette handler is therefore able to lift individual storage cassettes from their cassette locations and to lower them back to the cassette locations. Raised cassettes can be held in the upper section by means of the cassette holder, which can form part of the cassette lift or be a device separate from the cassette lift. Further, the transport mechanism allows to horizontally move a cassette held by the cassette holder from a position above its cassette location to a position where the cassette is located adjacent to the opening in the vertical insulating wall. And the transport mechanism can also move the cassette back from the position adjacent to said opening to the position above its cassette location, from where it can be lowered back into the cassette location.

When a cassette is at the position adjacent to the opening in the insulating wall, the objects therein can be accessed quickly and efficiently, and this at a higher temperature than the storage temperature.

Advantageously, the cassette handler further comprises a cassette housing horizontally enclosing a cassette space for receiving at least part of a cassette raised by said lift. This cassette housing comprises an open section at one vertical side of the cassette space. The open section faces the access opening in the access position of the cassette holder. Hence, in the access position, the cassette space is shielded towards the storage chamber by the cassette housing, while the cassette is accessible through the access opening and the open section.

In another advantageous embodiment, the storage device comprises a plurality of signal lights arranged vertically along the access opening. These lights can be used for highlighting the vertical location to be accessed in a cassette held by the lift when said cassette holder is in said access position.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

MODES FOR CARRYING OUT THE INVENTION

Definitions

A "low-temperature storage device" is a storage device adapted to store objects at temperatures below 0° C., in particular below −20° C., advantageously between −90° C. and −60° C.

A "plate spring" is a spring having a sheet-like, elastic body that is designed to be bent to varying curvatures against an elastic force. In most embodiments, the elastic body is, in a relaxed position, arranged in a plane, i.e. flat.

Figure 1:
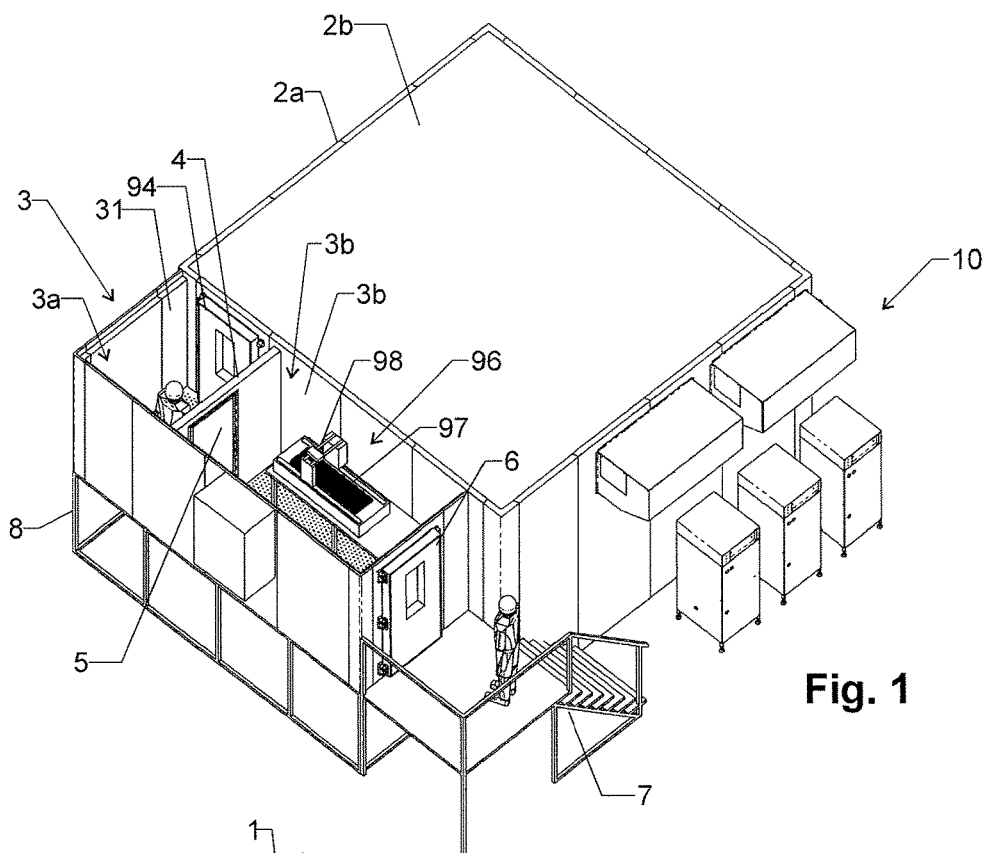
FIG. 1 shows a view of a storage device, with the ceiling of the transfer chamber removed.
Figure 2:
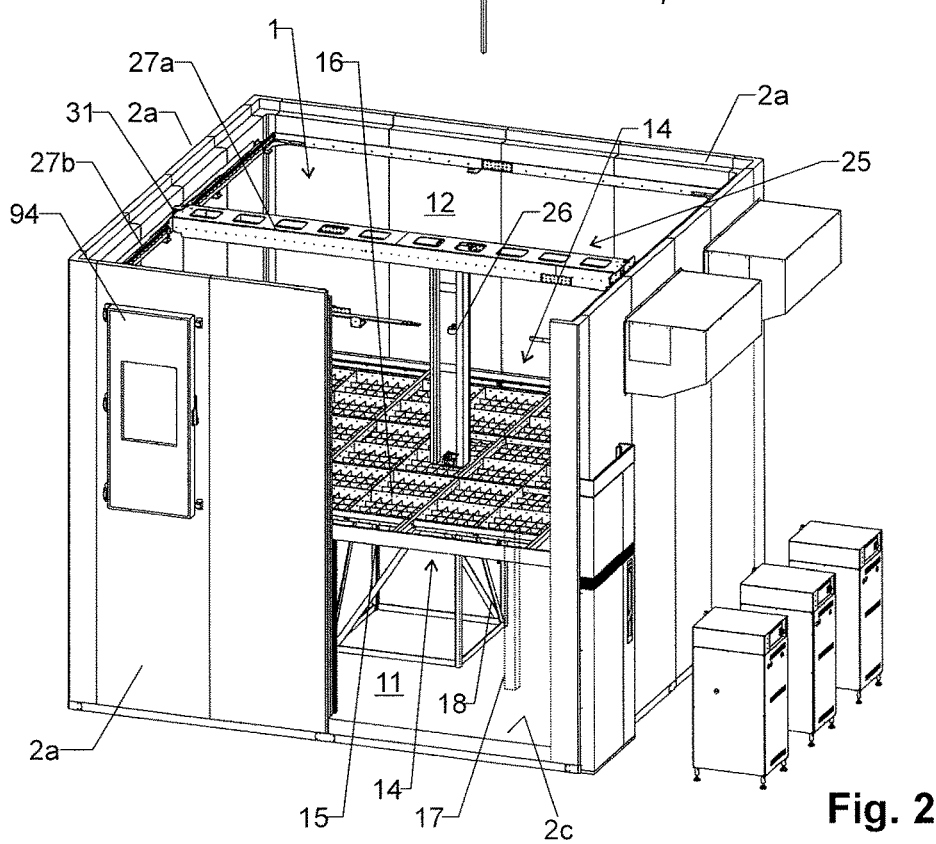
FIG. 2 shows a device similar to the device of FIG. 1 without the transfer chamber and with some of the walls of the storage chamber removed.
Figure 3:
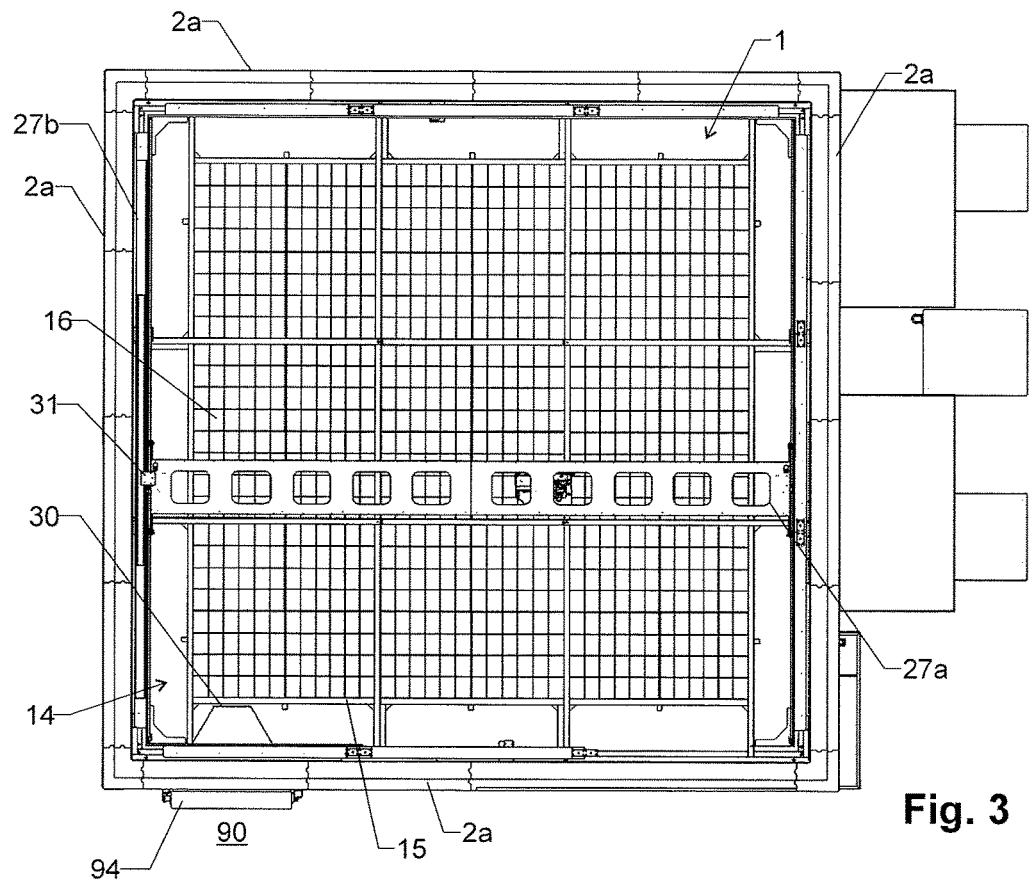
FIG. 3 shows the device of FIG. 2 from above.

Overview:

An embodiment of a storage device is shown in FIGS. 1-3. It comprises a storage chamber 1 enclosed by vertical insulating side walls 2a, an insulating ceiling 2b and an insulating floor 2c.

A transfer chamber 3 (FIG. 1) is located adjacent to storage chamber 1 and shares at least one of the insulating side walls 2a with storage chamber 1. In the embodiment of FIG. 1, transfer chamber 3 is divided into two sub-chambers 3a, 3b with a separating wall 4 having a lock door 5 arranged between them, but transfer chamber 3 can also be a single chamber.

A door 6 provides user access to transfer chamber 3. In the embodiment of FIG. 1, stairs 7 lead up to door 6 because transfer chamber 3 is above the level of bottom wall 2c of the device. For the same reason, transfer chamber 3 is supported by struts 8 at its bottom side.

A refrigerator device 10 is provided to cool storage chamber 1 to a storage temperature below 0° C., in particular below −20° C. Typically, the storage temperature is in the range of −90° C. to −60° C. Refrigerator device 10 also cools transfer chamber 3 to a transfer temperature below 0° C., in particular at approximately −20° C.

Storage Chamber:

The storage chamber 1 shown here is of cuboid shape. As best seen in FIG. 2, it is divided into a bottom section 11 and a top section 12. For reasons that will become apparent, top section 12 comprises typically 50-70% of the volume of storage chamber 1, and bottom section 11 the rest.

Bottom section 11 holds a cassette store 14 formed by a gridding 15 located at the top of bottom section 11. Gridding 15 forms an array of rectangular apertures 16. Each rectangular aperture 16 forms a cassette location for receiving a storage cassette. One such storage cassette 17 is shown in dotted lines in FIG. 2.

The gridding of cassette store 14 is mounted at a fixed height, e.g. by means of a central arrangement of struts 18 as well as by suitable lateral supports along its periphery (not shown).

Figure 7:
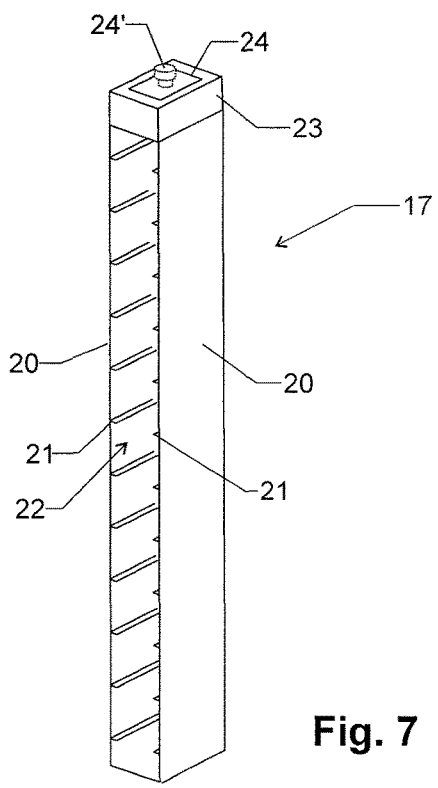
FIG. 7 shows a single storage cassette.
Figure 9:
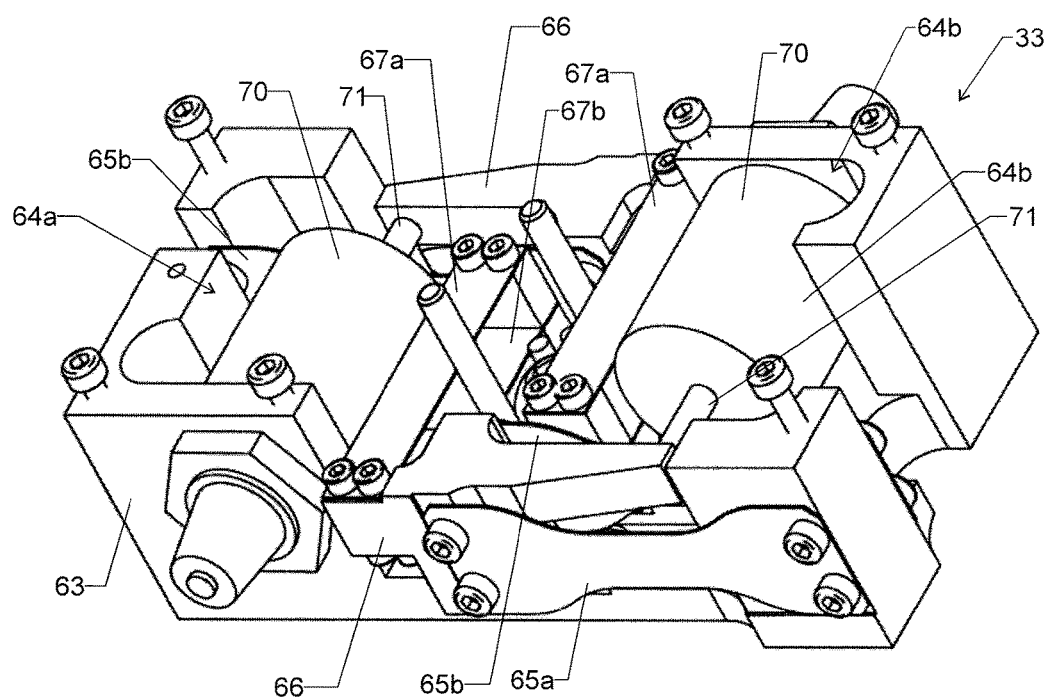
FIG. 9 shows a second embodiment of a cassette holder.

An example of a storage cassette 17 is shown in FIG. 7. It comprises two vertical sidewalls 20, with ledges 21 formed thereon. The ledges form storage locations 22 for receiving the objects to be stored. At its top end, the storage cassette 17 comprises an insulating head section 23. The head sections of all storage cassettes 17 inserted into cassette store 14 form an insulating wall between bottom section 11 and top section 12 of storage chamber 1, thereby helping to maintain a more constant temperature in bottom section 11 where most of the objects are stored.

A metal plate 24 or a coupling 24' (shown in dotted lines) is located at the top of each storage cassette 17, whose purpose will be described below.

The individual cassette locations or apertures 16 in cassette store 14 have a size fitting the footprint of the storage cassettes 17 to be received. As best seen in FIG. 3, the embodiment of the device shown in FIGS. 1-3 has a cassette store 14 adapted to receive storage cassettes 17 of rectangular footprint, e.g. of 134×86 mm, such that the storage cassettes can be dimensioned to receive objects having the standardized SBS dimensions of 127.75×85.48 mm.

Figure 6:
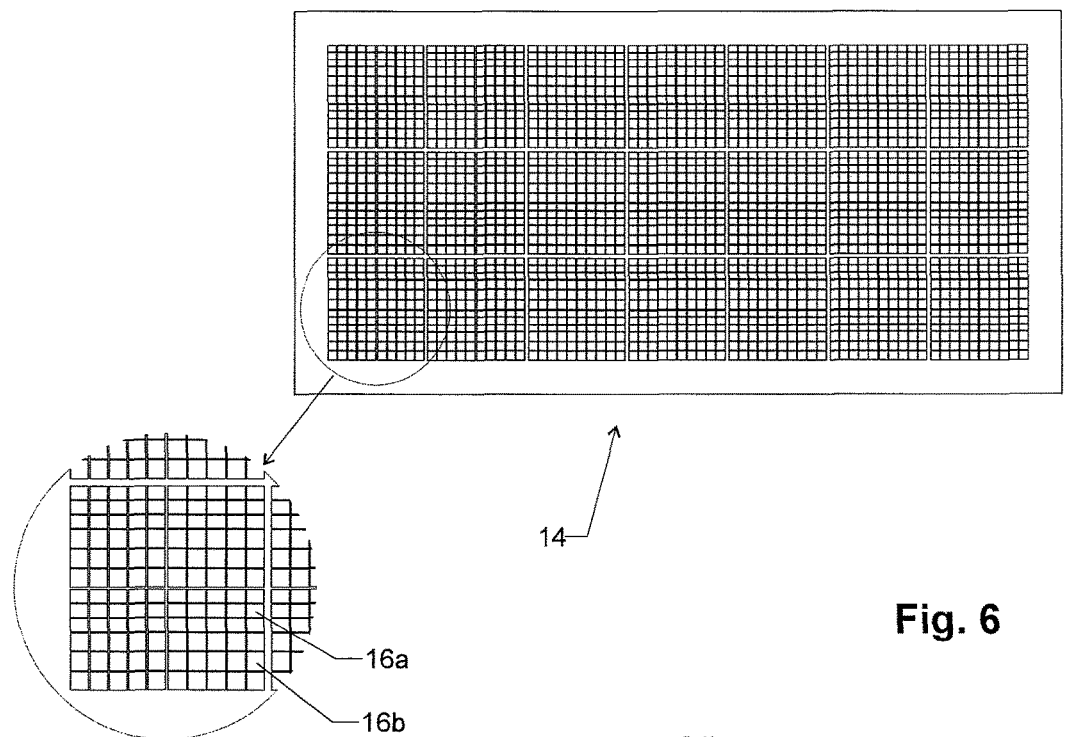
FIG. 6 shows a top view of the cassette store of a larger embodiment of the device.

In another advantageous embodiment, cassette store 14 is designed to receive at least two types of storage cassettes having different footprints. FIG. 6 shows an example for such a cassette store 14 as seen from above, albeit a store for being mounted in a larger storage chamber than the one shown in FIGS. 2 and 3. This cassette store forms a plurality of first cassette locations 16a and of second cassette locations 16b, wherein the two types of cassette locations have different footprint. For example, the first type of cassette locations 16a has a rectangular footprint in the SBS format of 134×86 mm, while the second type of cassette locations 16b has a "cryobox" square footprint of 137×137 mm.

Cassette Handler:

As mentioned, and as best seen in FIG. 2, a cassette handler 25 is located in top section 12 of storage chamber 1. It comprises a cassette lift 26 adapted to move an individual storage cassette 17 between its cassette location 16 in cassette store 15 and top section 12. Further, cassette handler 25 comprises a cassette holder, which is advantageously formed by cassette lift 26, for holding a raised cassette in top section 12 of storage chamber 1.

Cassette lift 26, or at least the cassette holder, is arranged on a transport mechanism 27a, 27b, which is adapted to horizontally displace the cassette holder with a raised cassette, between a position where the raised cassette is vertically above its cassette location 16 to an access position where the raised cassette is adjacent to an access opening 30 (see FIGS. 3 and 4) of storage chamber 1.

In order to provide enough room for an upright storage cassette 17 as well as the overhead required by cassette handler 25, top section 12 of storage chamber 1 is advantageously somewhat higher than bottom section 11.

Transport mechanism 27a, 27b comprises a horizontal beam 27a spanning storage chamber 1 and being held at opposite ends by rails 27b. Beam 27a is located at the top of upper section 12. Cassette lift 26 is suspended from beam 27a. A displacement drive 31 is provided for horizontally displacing beam 27a along the rails 27b, and also for horizontally displacing cassette lift 26 along beam 27a.

Figure 5:
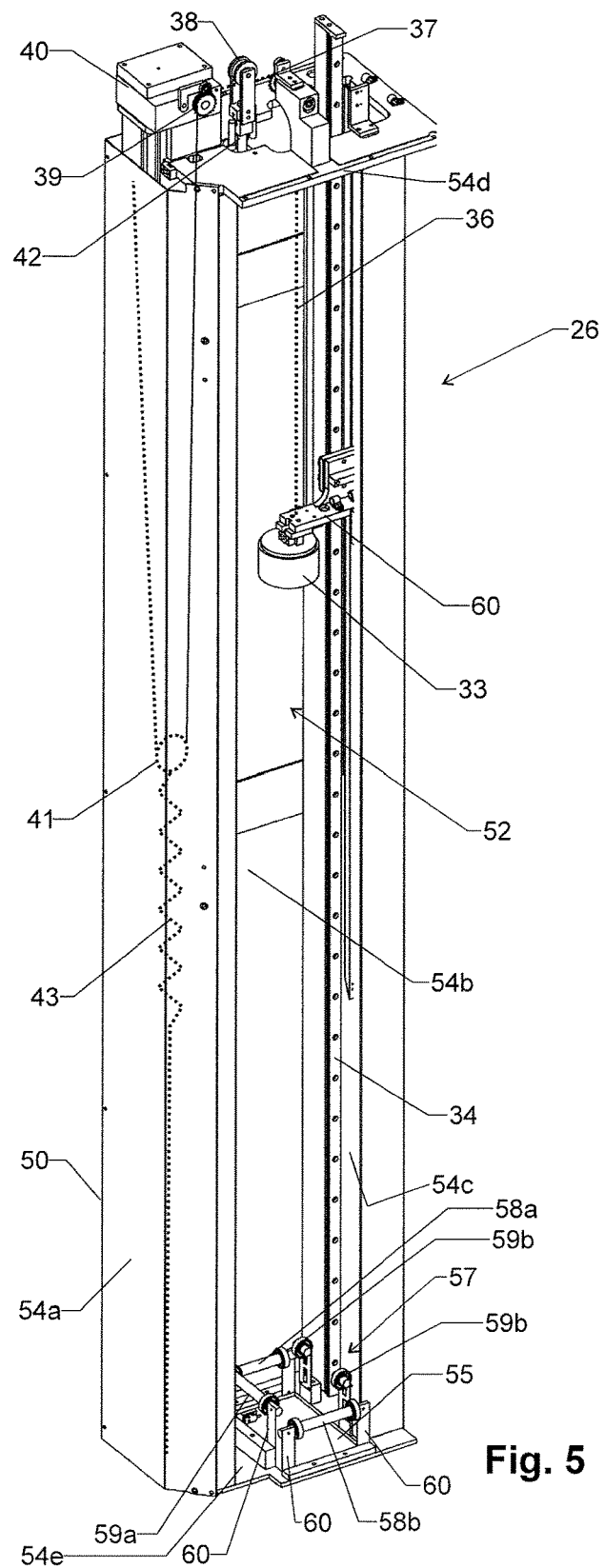
FIG. 5 shows part of the cassette handler.

Cassette lift 26 is shown in more detail in FIG. 5. It comprises the already mentioned cassette holder 33, which is, in the embodiment of FIG. 5, a magnetic cassette holder adapted to hold a storage cassette by its metal plate 24 (cf. FIG. 7).

Figure 8:
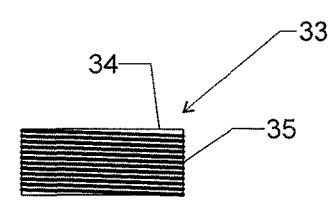
FIG. 8 shows a first embodiment of a cassette holder.

An advantageous embodiment of a magnetic cassette holder 33 is shown in FIG. 8. It comprises a permanent magnet 34 in combination with an electromagnet 35, with electromagnet 35 oriented to cancel, or at least reduce, the magnetic field of permanent magnet 34. In this manner, cassette holder 33 will firmly hold a storage cassette in the absence of a current through electromagnet 35, while a current is required to release the cassette. This design prevents an accidental release of the cassette in a power failure.

Turning back to FIG. 5, cassette lift 26 comprises a lift drive adapted to move cassette holder 33 along a vertical guide rail 34. This lift drive comprises a chain 36 attached at a first end to cassette holder 33. It extends upwards from cassette holder 33 to a first guide wheel 37 located at the top of cassette lift 26. At first guide wheel 37, chain 36 is redirected into a slight downward direction to a second guide wheel 38, and from there it is redirected into a slight upward direction to a sprocket 39 driven by a lift motor 40. At sprocket 39, chain 36 is redirected into a substantially vertical downward direction to a fourth guide wheel 41 and from there backwards up to be moored at its second end in the top of cassette lift 26.

A damped chain tightener is adapted to elastically pull second guide wheel 38 down and thereby to elastically urge it against chain 36.

A spring member 43 is adapted to pull third guide wheel 41 downwards, thereby keeping the section of chain 36 between sprocket 39 and its second end taught.

In operation, lift motor 40 drives sprocket 39, which in turn causes cassette holder 33 to be lifted or lowered. If a cassette lifted by cassette holder 33 gets temporarily stuck, e.g. on an ice formation, chain tightener 42 yields, thereby avoiding the generation of excessive forces in chain 36.

Figure 13:
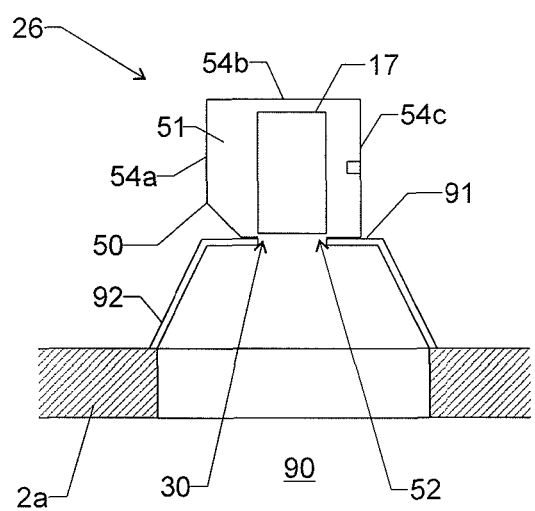
FIG. 13 shows a horizontal sectional view of the cassette lift at the access opening.

As shown in FIGS. 5 and 13, lift 26 comprises a cassette housing 50, which is located at a fixed vertical position and encloses a cassette space 51 which is intended to receive at least part, typically all, of a raised storage cassette. Cassette housing 50 comprises an open section 52 at one of its vertical sides. This open section 52 faces access opening 30 when cassette lift 26 and cassette holder 33 are in their access position. This will be described in more detail below.

Cassette housing 40 comprises three lateral side walls 54a, 54b, 54c closing cassette space 51 on three sides. Further, it comprises a top wall 54d (FIG. 5) closing cassette space 51 from above.

At the bottom of cassette lift 26, a bottom wall 54e is provided (FIG. 5), which closes the bottom of cassette space 51, except for a lift opening 55, whose size matches the footprint of the storage cassette to be handled by cassette lift 26. When the cassette is in its raised position, i.e. in cassette space 51, lift opening 55 is blocked by the cassette, thereby reducing an exchange of air at that location.

As can further be seen from FIG. 5, cassette lift 26 comprises a guiding device 57 for laterally guiding a storage cassette while it is being raised or lowered by cassette lift 26. Guiding device 57 is arranged at the bottom end of cassette lift 26, advantageously around lift opening 57.

In the embodiment of FIG. 5, guiding device 57 comprises a first pair of rollers 58a, 58b as well as a second pair of rollers 59a, 59b. Each pair of rollers comprises two rollers that can be rotated around respective horizontal roller axes. The roller axes of each pair extend parallel to each other and are spaced apart, by a distance exceeding a horizontal dimension of the cassette, so that the two rollers can run along opposite vertical sides of the cassette. The axes of the first pair of rollers 58a, 58b are perpendicular to the axes of the second pair of rollers (59a, 59b) such that the rollers can engage the cassettes from all four sides.

Each roller is held by at least one spring member 60, which is structured to elastically yield in horizontal direction, thereby keeping the rollers in contact with the surfaces of the cassette. In the embodiment of FIG. 5, each spring member is formed by a plate spring (flat spring) mounted to bottom wall 54e.

In the embodiment of FIG. 5, two pairs of such rollers are provided. If the cassette requires guidance primarily along one direction only, a single pair of rollers can be used.

Guiding device 57 is located at a fixed vertical position within storage chamber 1.

Alternative Cassette Holder:

In the embodiment of FIG. 8, a magnetic cassette holder 33 has been shown. FIGS. 9-12 show a mechanical embodiment of such a holder. This holder is suspended, alternatively to the magnetic holder, on the same trolley 60 (FIG. 5) of cassette lift 26. For this purpose, a cover plate 61 (only shown in FIG. 10) is provided with a suitable adaptor stub 62 at its top side.

The cassette holder of this second embodiment comprises a rigid frame 63. It further comprises two engaging mechanisms 64a, 64b that are of identical design and arranged symmetrically around a center of the holder.

Each engaging mechanism 64a, 65b comprises a first pair of parallel plate springs 65a, 65b arranged at a distance from each other, with the sheet-like bodies of the springs aligned vertically (i.e. parallel to the longitudinal axis of the storage cassette 17 to be picked up). The first ends of the plate springs 65a, 65b are mounted to frame 63, while the second ends are mounted to a link body 66. Due to its suspension by the plate springs 65a, 65b, link body 66 can substantially move along one horizontal line only.

The first ends of a second pair of parallel plate springs 67a, 67b are mounted to link body 66. The sheet-like bodies of the second pair of plate springs 67a, 67b are aligned horizontally. The second ends of these springs are attached to a gripper body 68. Hence, gripper body 68 is displaceable along one vertical line in respect to link body 66, and along a vertical plane in respect to frame 63.

A magnetic actuator 70 is arranged in frame 63. It comprises a pusher 71, which is in a retracted position when no current is applied to actuator 70 (as shown in FIG. 12), and in an extended position (FIG. 11) when a current is applied. Upon applying a current, pusher 71 pushes link body 62 against the force of the first pair of plate springs 65a, 65b from the position of FIG. 12 into the position of FIG. 11, thereby moving gripper body 68 along arrow A of FIG. 11.

Figure 11:
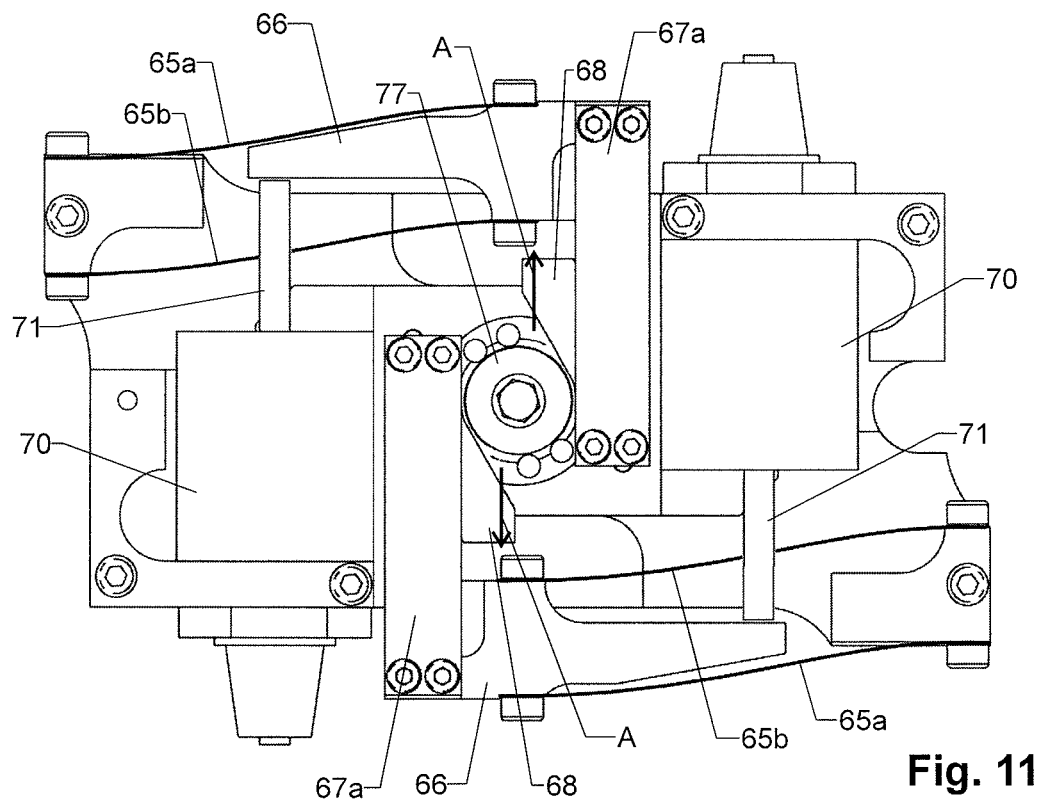
FIG. 11 shows the embodiment of FIG. 9 in its open position from above.
Figure 12:
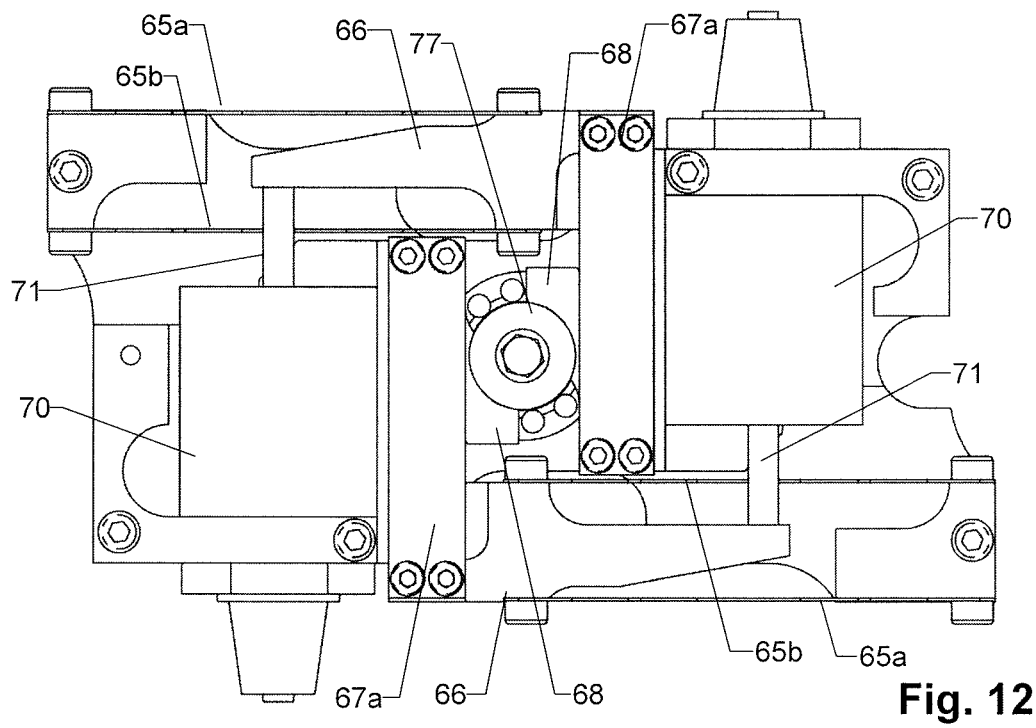
FIG. 12 shows the embodiment of FIG. 9 in its closed position from above.

By operating both actuators 70 of the engaging mechanisms 64a, 64b at the same time, both gripper bodies 68 are moved from their positions in FIG. 12 to their positions in FIG. 11.

Figure 10:
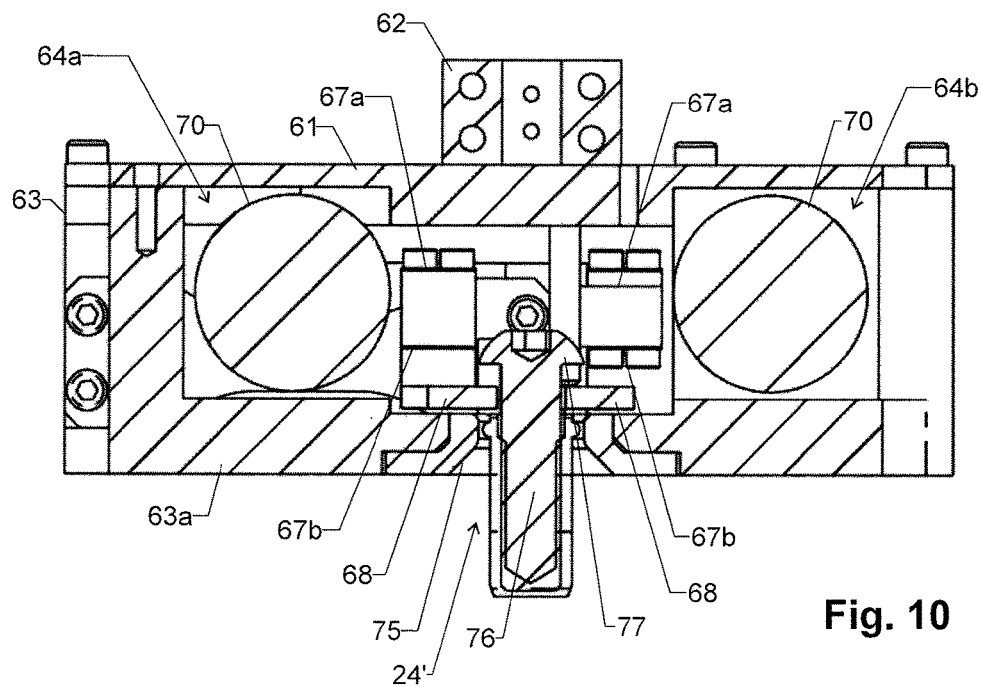
FIG. 10 shows a sectional view of the embodiment of FIG. 9.

As best seen in FIG. 10, frame 63 comprises an opening 75 at its bottom side, which has a diameter sufficient to receive coupling 24' of a storage cassette 17 (cf. FIG. 7, where coupling 24' is shown in dotted lines). Coupling 24' projects over the top side of storage cassette 17 and comprises a neck 76 and a head 77 at the top of neck 76, with head 77 projecting laterally beyond head 76.

When coupling 24' is inserted in opening 75, the gripper bodies 68 can engage the coupling 24' below head 77 from both sides when they are in their closed position 77 as shown in FIG. 12, while they release head 77 when moved to their opened position as shown in FIG. 11.

When the gripper bodies 68 have engaged head 77 of coupling 24' and the cassette is lifted by vertically moving the whole cassette holder, the weight of the cassette will pull the gripper bodies 68 downwards (against the resilient forces of the second pairs of plate springs 67*a*), until the gripper bodies 68 come to rest against a bottom support 63*a* of frame 63, such that the weight can be transferred directly to frame 63 and does not have to be carried by the mechanically more sensitive parts of the engaging mechanisms 64*a*, 64*b*.

As in the first embodiment, the second embodiment of the cassette holder 33 is designed such that it safely engages the storage cassette in the absence of electrical power, and electrical power is required for releasing the storage cassette, which again avoid accidents in case of a power failure.

Hence, in more general terms, the cassette holder 33 of this second embodiment comprises:

A frame 63 forming a support 63*a*;

At least two gripper bodies 68 arranged above the support 63*a* and mounted to be resiliently displaced, advantageously by at least 2 mm, in vertical direction in respect to the frame 63; and At least one engaging mechanism 64*a*, 64*b* adapted and structured for displacing the gripper bodies 68 against the coupling 24' of one of the storage cassettes inserted into the frame 63, thereby engaging this coupling (24').

The cassette holder 33 is adapted and structured such that the weight of the storage cassette 17, whose coupling 24' is engaged by the gripper bodies 68, pulls the gripper bodies 68 down to rest against the support 63*a*.

Figure 4:
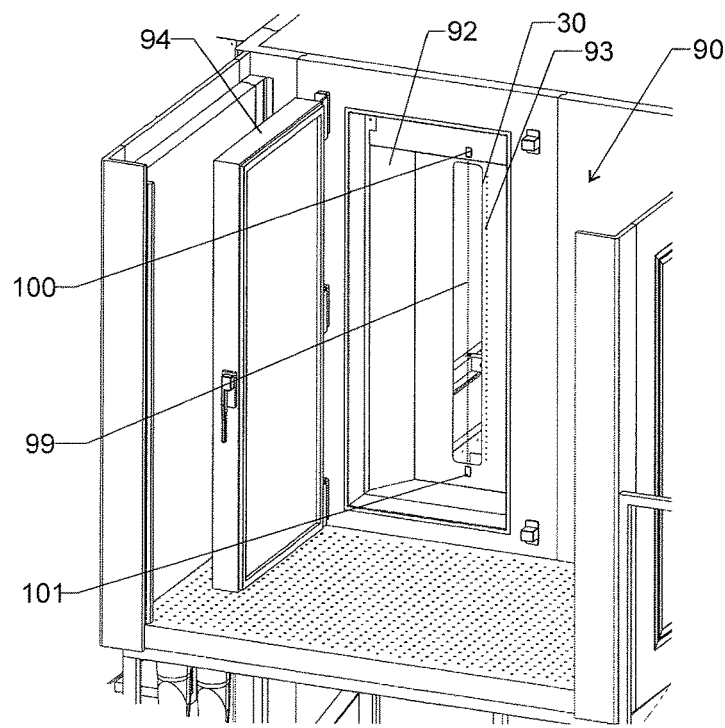
FIG. 4 shows a view of the access opening and its door.

Access Opening:

As mentioned, and as can be seen in FIGS. 3 and 4, an access opening 30 is arranged in one of the vertical insulating walls 2*a* of storage chamber 1. Access opening 30 is located between storage chamber 1 and a transfer location 90 outside storage chamber 1.

FIG. 13 shows the situation when cassette handler 25 brings cassette holder 33 holding a storage cassette 17 to its access position. In this position, storage cassette 17 if adjacent to access opening 30, such that the storage locations 22 in storage cassette 17 can be accessed through access opening 30.

As can be seen, cassette housing 50 with its walls 54*a*, 54*b*, 54*c* is, in this position, located such that its open section 52 faces access opening 30, and housing 50 comes into contact with a frame 91 of access opening 30. Thereby, a sealed connection is formed between access opening 30 and cassette space 51. In this context, the term "sealed connection" does not necessarily imply that the connection is truly gas tight. However, the gap between cassette housing 50 and docking section 91 should be no more than 20 mm, in particular no more than 1 mm.

The height of access opening 30 advantageously corresponds to at least the combined height of all storage locations 22 of one storage cassette 17. Further, in the access position, all storage locations 22 of storage cassette 17 held by cassette holder 33 are accessible through access opening 30. In this way, every object in the storage cassette can be accessed easily and quickly.

The width of access opening 30 should be larger, but advantageously not more than 20% larger, than the width of the storage locations 22 and/or than the width of the objects stored therein.

In the embodiment of FIG. 13, frame 91 of access opening 30 is formed by a bay 92 extending from insulating wall 2*a* into storage chamber 1.

As can be seen from FIG. 4, a vertical line of signal lights 93 is located along an edge of access opening 30. As mentioned, these signal lights 93 can be used for highlighting the vertical location to be accessed in a storage cassette 17 held in the lift when cassette holder 33 is in said access position. They can e.g. be controlled by a control unit that keeps track of the objects stored within storage chamber 1.

In the embodiment of FIG. 4, a light barrier 99 comprising a laser light source 100 and a light receiver 101 extends vertically over access opening 30. It is used for detecting objects that are not completely inserted into their respective object location 22 in storage cassettes 17 and issue a warning if this is the case.

Also as best seen from FIG. 4, an access door 94 can be provided for closing access opening 30 when it is not in use. By closing this door, an air exchange (and in particular the entry of unwanted humidity into storage chamber 1) can be prevented, which is of particular advantage when cassette lift 26 moves away from access opening 30.

Transfer Chamber:

Even though transfer location 90 can be located completely outside the storage device, it is advantageously positioned in a transfer chamber 3 (see FIG. 1). In order to further reduce heat transfer and the entry of humidity into storage chamber 1, transfer chamber 3 can be cooled by means of refrigerator device 10. The temperature within transfer chamber 3 is advantageously below 0° C. but above the storage temperature in storage chamber 1. Typically, the temperature in transfer chamber 3 is around −20° C.

As shown in FIG. 1 and as already disclosed, transfer chamber 3 can be divided into two sub-chambers 3*a*, 3*b* with a separating wall 4 having a lock door 5 arranged between them. This allows to form an airlock that further improves the insulation of storage chamber 1.

As also can be seen from FIG. 1, various equipment for working on the samples or objects stored in storage chamber 1 can be located in transfer chamber 3. Placing such equipment there allows to operate it at only moderately low temperatures, thereby improving equipment reliability and user accessibility.

As one particularly advantageous example, such equipment can comprise an item picker 96, which can be used when the stored objects are containers containing individual items, such as tube holders holding sample tubes. Item picker 96 is adapted and structured to remove and/or insert individual items from/into the objects, e.g. for sorting, assembling, individually removing or individually adding them. Such an item picker, which is of a generally known design, typically comprises an item picker location 97 for receiving at least one of the objects to be stored in the storage cassettes, as well as a picker device 98 with a gripper or similar structure that can handle the items in the object. In particular, picker device 98 can be structured and adapted for removing an individual item from a plurality of items in an object at picker location 97 and/or for adding an individual item to a plurality of items in the object at said picker location 97.

Notes:

As can be seen from FIG. 2, storage chamber 1 forms advantageously a single, horizontally undivided space, which makes it easy to cool it by means of cooling aggregates arranged e.g. along the insulating walls. However, storage chamber 1 may also have vertical dividing walls arranged therein.

For handling different types of storage cassettes 17, in particular types that have different footprint as mentioned above in reference to FIG. 6, at least two separate cassette lifts 26 can be used, each one tailored to one type of storage cassettes. Alternatively, a single cassette lift can be used if guiding device 57 is adjustable in size.

While there are shown and described presently preferred embodiments of the invention, it is to be distinctly understood that the invention is not limited thereto but may be otherwise variously embodied and practiced within the scope of the following claims.

The invention claimed is:

1. A low-temperature storage device for storing a plurality of objects, said device comprising:
   a storage chamber having a bottom section and a top section,
   a refrigerator device adapted and structured to cool said storage chamber to a storage temperature below 0° C.,
   vertical insulating walls enclosing said storage chamber,
   a transfer location arranged outside said storage chamber,
   an access opening arranged above the bottom section and in at least one of said insulating walls between said storage chamber and said transfer location,
   a cassette store arranged in said bottom section of said storage chamber and forming a plurality of cassette locations,
   a plurality of storage cassettes arranged beside each other in said cassette locations, wherein each storage cassette comprises a plurality of storage locations arranged vertically above each other, wherein each storage location is structured and adapted to receive at least one of said objects,
   a cassette handler located in said storage chamber comprising;
   a) a cassette lift adapted and structured to move an individual storage cassette between its cassette location and said top section,
   b) a cassette holder adapted and structured to hold a storage cassette raised by the cassette lift in a raised position in said top section, said cassette holder having a side access interface opening that can be positioned adjacent to the access opening, and
   c) a transport mechanism structured and adapted to horizontally displace said cassette holder, with a raised storage cassette, between a position where said raised storage cassette is vertically above its cassette location to an access position where said raised storage cassette in said raised position is adjacent to said access opening such that the storage locations of said storage cassette in said raised position are accessible through said access opening,
   wherein the storage locations are accessible when the side access interface is located adjacent the access opening.

2. The device of claim 1 wherein said cassette handler further comprises a cassette housing horizontally enclosing a cassette space for receiving at least part of a storage cassette raised by said cassette lift, wherein said cassette housing comprises an open section at one vertical side, which open section faces said access opening in said access position of said cassette holder.

3. The device of claim 2 wherein said cassette housing further closes said cassette space from above.

4. A low-temperature storage device for storing a plurality of objects, said device comprising:
   a storage chamber having a bottom section and a top section,
   a refrigerator device adapted and structured to cool said storage chamber to a storage temperature below 0° C.,
   vertical insulating walls enclosing said storage chamber,
   a transfer location arranged outside said storage chamber,
   an access opening arranged above the bottom section and in at least one of said insulating walls between said storage chamber and said transfer location,
   a cassette store arranged in said bottom section of said storage chamber and forming a plurality of cassette locations,
   a plurality of storage cassettes arranged beside each other in said cassette locations, wherein each storage cassette comprises a plurality of storage locations arranged vertically above each other, wherein each storage location is structured and adapted to receive at least one of said objects,
   a cassette handler located in said storage chamber comprising;
   a) a cassette lift adapted and structured to move an individual storage cassette between its cassette location and said top section,
   b) a cassette holder adapted and structured to hold a storage cassette raised by the cassette lift in a raised position in said top section, said cassette holder having a side access interface opening that can be positioned adjacent to the access opening, and
   c) a transport mechanism structured and adapted to horizontally displace said cassette holder, with a raised storage cassette, between a position where said raised storage cassette is vertically above its cassette location to an access position where said raised storage cassette is adjacent to said access opening;
   said cassette handler further comprises a cassette housing horizontally enclosing a cassette space for receiving at least part of a storage cassette raised by said cassette lift, wherein said cassette housing comprises an open section at one vertical side, which open section faces said access opening in said access position of said cassette holder,
   wherein said cassette housing has a lift opening at a bottom side of said cassette space, wherein said lift opening is blocked by a storage cassette when said storage cassette is raised into said cassette space, and
   wherein the storage locations are accessible when the side access interface is located adjacent the access opening.

5. The device of claim 2, wherein, in said access position of said cassette holder, said cassette housing is in contact with a frame of said access opening, thereby forming a sealed connection between said access opening and said cassette space.

6. A low-temperature storage device for storing a plurality of objects, said device comprising:
   a storage chamber having a bottom section and a top section,
   a refrigerator device adapted and structured to cool said storage chamber to a storage temperature below 0° C.,
   vertical insulating walls enclosing said storage chamber,
   a transfer location arranged outside said storage chamber,
   an access opening arranged above the bottom section and in at least one of said insulating walls between said storage chamber and said transfer location,
   a cassette store arranged in said bottom section of said storage chamber and forming a plurality of cassette locations,
   a plurality of storage cassettes arranged beside each other in said cassette locations, wherein each storage cassette comprises a plurality of storage locations arranged vertically above each other, wherein each storage location is structured and adapted to receive at least one of said objects,
a cassette handler located in said storage chamber comprising;
a) a cassette lift adapted and structured to move an individual storage cassette between its cassette location and said top section,
b) a cassette holder adapted and structured to hold a storage cassette raised by the cassette lift in a raised position in said top section, said cassette holder having a side access interface opening that can be positioned adjacent to the access opening, and
c) a transport mechanism structured and adapted to horizontally displace said cassette holder, with a raised storage cassette, between a position where said raised storage cassette is vertically above its cassette location to an access position where said raised storage cassette is adjacent to said access opening; and
a plurality of signal lights arranged vertically along said access opening for highlighting a vertical location to be accessed in a storage cassette held by said cassette holder when said cassette holder is in said access position,
wherein the storage locations are accessible when the side access interface is located adjacent the access opening.

7. The device of claim 1 wherein said cassette store forms a plurality of first cassette locations and of second cassette location, wherein said first and second cassette locations have different footprints.

8. The device of an claim 1 wherein said cassette handler comprises, at a fixed vertical position, a guiding device for laterally guiding a storage cassette while being raised or lowered by said cassette lift, wherein said guiding device comprises at least one pair of spaced-apart rollers having parallel axes of rotation, and wherein each roller is held by at least one spring member and adapted to elastically yield in horizontal direction.

9. The device of claim 8 further comprising at least a first and a second pair of spaced-apart rollers, wherein the roller axes of said first pair are perpendicular to the roller axes of said second pair.

10. The device of claim 1, wherein said storage cassettes comprise couplings projecting over a top side of each storage cassette, wherein said cassette holder comprises
a frame forming a support,
at least two gripper bodies arranged above said support and mounted to be resiliently displaced in vertical direction in respect to said frame, and
at least one engaging mechanism adapted and structured for displacing said gripper bodies against the coupling of one of said storage cassettes inserted into said frame, thereby engaging said coupling,
wherein said cassette holder is adapted and structured such that a weight of the storage cassette, whose coupling is engaged by said gripper bodies, pulls said gripper bodies down to rest against said support.

11. The device of claim 1, wherein said cassette holder comprises a permanent magnet and an electromagnet, wherein said electromagnet is oriented to cancel or at least reduce a magnetic field of said permanent magnet and wherein said cassette holder is adapted to firmly hold a storage cassette in an absence of a current through said electromagnet.

12. The device of claim 1 wherein said cassette lift further comprises a lift drive for lifting said cassette holder, wherein said lift drive comprises
a lift motor driving a sprocket,
a first guide wheel,
a second guide wheel, and
a chain attached to said cassette holder, extending upwards from said cassette holder to said first guide wheel, and extending from said first guide wheel to said second guide wheel and from there to said sprocket, and
a chain tightener adapted and structured to elastically urge said second guide wheel against said chain.

13. The device of claim 1 wherein a height of said access opening is at least equal to a combined height of all storage locations of one storage cassette, and wherein, in said access position of said cassette holder, all storage locations of the storage cassette held by said cassette holder are accessible through said access opening.

14. The device of claim 1 further comprising an access door closing said access opening.

15. The device of claim 1 further comprising a transfer chamber surrounding said transfer location, wherein said refrigerator device is adapted and structured to cool said transfer chamber to a transfer temperature below 0° C. but above said storage temperature.

16. The device of claim 15 further comprising an item picker arranged in said transfer chamber, wherein said item picker comprises:
an item picker location for receiving said at least one of said objects to be stored in said storage cassettes, and
a picker device structured and adapted for removing an individual item from a plurality of items in said at least one of said objects at said picker location and/or for adding an individual item to a plurality of items in said at least one of said objects at said picker location.

17. The device of claim 1 further comprising a light barrier extending over said access opening adapted and structured to detect objects not completely inserted into their storage location.

18. The device of claim 1, wherein the refrigerator device is adapted and structured to cool said storage chamber to a storage temperature below −20° C.

19. The device of claim 1, wherein the cassette lift has an open vertical side that can be positioned alongside the access opening.

20. The device of claim 1, wherein the cassette lift has an upper end, a lower end, plural vertical sides and an open vertical side that can be positioned alongside the access opening.

* * * * *